United States Patent [19]

Nagel et al.

[11] Patent Number: 4,963,689

[45] Date of Patent: Oct. 16, 1990

[54] HETEROCYCLICGUANIDINES AS 5HT$_3$ ANTAGONISTS

[75] Inventors: Arthur A. Nagel; James P. Rizzi; Terry J. Rosen, all of Groton, Conn.

[73] Assignee: Pfizer Inc., New York, N.Y.

[21] Appl. No.: 349,189

[22] Filed: May 19, 1989

[51] Int. Cl.$^5$ .................. C07D 277/28; C07D 417/04
[52] U.S. Cl. .................................. 548/181; 548/205; 548/240; 548/504; 549/65; 549/497
[58] Field of Search ............... 548/181, 205, 240, 504; 549/65, 492

[56] References Cited

U.S. PATENT DOCUMENTS 4,260,628  4/1981  Jonas ................................. 548/491
4,563,527  1/1986  Fujii ................................. 546/169

OTHER PUBLICATIONS

Nesi, J. Chem. Soc., Perkin Trans. 7(9), 1871, 1985.

*Primary Examiner*—Robert Gerstl
*Attorney, Agent, or Firm*—Peter C. Richardson; J. Trevor Lumb; James M. McManus

[57] ABSTRACT

Heterocyclicguanidines as 5HT$_3$ antagonists useful in the treatment of nausea, anxiety, pain, schizophrenia and gastrointestinal disorders.

9 Claims, No Drawings

HETEROCYCLICGUANIDINES AS 5HT₃ ANTAGONISTS

BACKGROUND OF THE INVENTION

This invention relates to novel heterocyclicguanidines which are antagonists at the serotonin 5HT₃ receptor and useful as anti-emetic agents in warm blooded animals, particularly the emesis caused by administration of the anticancer drug cisplatin. In addition, the compounds of the present invention are useful in the treatment of schizophrenia, anxiety, pain and gastrointestinal disorders.

Compounds recognized for their ability to act as antagonists at the serotonin 5HT₃ receptor sites are described in U.S. Pat. Nos. 4,593,034 and 4,749,718 and U.K. patent application Nos. 2,125,398A, 2,166,726A, 2,166,727A, 2,166,728A and 2,193,633A.

SUMMARY OF THE INVENTION

The novel heterocyclicguanidines of the present invention are of formula I:

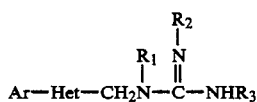

or a pharmaceutically acceptable acid addition salt thereof, wherein Ar is naphthyl, indol-3-yl, 2-methylindol-3-yl, 1-methylindol-3-yl, 1-benzylindol-3-yl, phenyl or mono- or disubstituted phenyl wherein said substituent is each lower alkyl, lower alkoxy, chloro, fluoro or bromo; Het is thiazolyl, furyl, thienyl, or isoxazolyl; $R_1$ is hydrogen or methyl; $R_2$ and $R_3$ when considered separately are each hydrogen, hydroxyethyl, alkyl of one to six carbon atoms, cycloalkyl of three to six carbon atoms or acetyl; and $R_2$ and $R_3$ when taken together are alkylene of two to three carbon atoms.

A preferred group of compounds are those wherein Het is thiazolyl and $R_1$, $R_2$ and $R_3$ are each hydrogen. Especially preferred within this group are the compounds 2-(guanidinomethyl)-4-(1'-methylindol-3'-yl)thiazole, 2-(guanidinomethyl)-4-(o-methoxyphenyl)thiazole, 2-(guanidinomethyl)-4-(2'-methylindol-3'-yl)thiazole, 2-(guanidinomethyl)-4-(indol-3'-yl)thiazole, 2-(guanidinomethyl)-4-phenylthiazole, 2-(indol-3'-yl)-4-(guanidinomethyl)thiazole and 2-(guanidinomethyl)-4-(o-fluorophenyl)thiazole.

DETAILED DESCRIPTION OF THE INVENTION

The compounds of the present invention can be prepared by the reaction of an aminomethylheterocyclic starting material and a S-methylthiopseudourea as follows

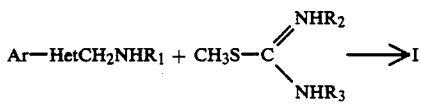

In practice, about equal moles of the amine and the thiourea (as an addition salt) are combined in a reaction-inert solvent, such as a lower alkanol, and allowed to react at from room temperature to the reflux temperature of the solvent until the evolution of methyl mercaptan has ceased. If an acid addition salt of the starting amine is employed, it is preferred that an equimolar amount of a base, such as sodium acetate, be added to the reactants in the reaction-inert solvent at the beginning of the reaction.

Reaction time is dependent on the reaction temperature and the inherent reactivity of the starting reagents. In general, at room temperature the reaction is complete after 12-24 hours, while at the reflux temperature of the solvent the reaction time is 1-6 hours.

The product, as an acid addition salt, can be isolated by concentrating the reaction solvent until the product commences to separate or the reaction mixture can be added to water, made basic and the product as a free base extracted with a water-immiscible solvent, such as methylene chloride or ethyl acetate.

A second approach to the synthesis of the compounds of the present invention comprises the reaction of $R_2$ (or $R_3$)—NH₂ with a N-cyano-S-methylthiopseudourea shown as follows:

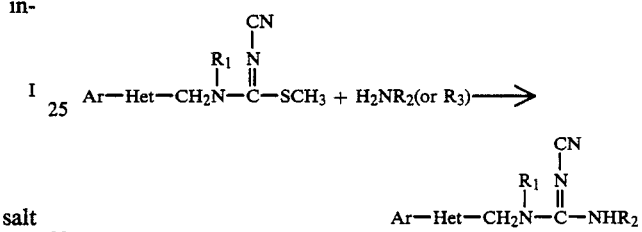

The N-cyano guanidine is then hydrolyzed by refluxing in concentrated hydrochloric acid to give I.

The hydrolysis is carried out at room temperature for six to ten hours. The reaction mixture can be concentrated to provide the product as an acid addition salt or the residual product can be treated with aqueous base and the free base I extracted with a water-immiscible solvent.

Compounds of the present invention wherein $R_2$ or $R_3$ are acetyl are prepared by diacylation providing compounds where both $R_2$ and $R_3$ are acetyl. Subsequently, one of the acetyl groups is hydrolyzed using aqueous sodium hydroxide in a water-miscible solvent such as tetrahydrofuran or methanol.

Compounds of the present invention can be purified by conventional means. Recrystallization from an appropriate solvent or flash column chromatography are the favored methods.

The free base products of the present invention can be converted to a salt by treating a solution of said product with at least an equimolar amount of the appropriate acid. The use of two moles of acid per mole of free base product can result in the formation of a double salt, i.e., a dihydrochloride, depending on the nature of Het.

The intermediates used in the synthesis of the compounds of the present invention are described herein or can be prepared by procedures which are available or suggested by the literature.

As previously mentioned, the compounds of the instant invention are antagonists of 5-hydroxytryptamine (5HT) at the 5HT₃ receptors. This is demonstrated by their ability to antagonize the effects of 5HT in the Bezold-Jarisch reflex [Richardson, et al., Nature 316, 126 (1985)] and their ability to bind to 5HT receptors in brain tissue [Watling, et al., European J. Pharmacol. 149, 397 (1988)]. The compounds of the present invention are especially useful in controlling emesis due to administration of platinum anti-cancer agents. Evaluation of these compounds as anti-emetic agents against cisplastin uses the procedure in Cylys, Res. Commun. Chem. Pathol. Pharmacol., 23, 61 (1979).

The compounds of the present invention can be administered as antiemetic agents by either the oral or parenteral routes of administration, with the former being preferred for reasons of patient convenience and comfort. In general, these antiemetic compounds are normally administered orally in dosages ranging from about 5 mg to about 10 mg per kg of body weight per day and 0.1 mg to about 1.0 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

EXAMPLE 1

2-(Guanidinomethyl)-4-(indol-3'-yl)thiazole (Ar=indol-3-yl; Het=thiazolyl; and $R_1$, $R_2$ and $R_3$=H A. N-acetylaminothioacetamide Into a cold (0° C.) solution of 34.6 g of N-acetylaminoacetonitrile and 45.5 ml of ammonium hydroxide in 135 ml of ethanol was bubbled hydrogen sulfide gas for about twenty minutes. The reaction mixture was allowed to warm to room temperature and was stirred overnight. The solvent was removed in vacuo and the residual brown oil purified by flash column chromatography using methanol-chloroform (1:9-v:v) on 500 g of silica gel. This provided the desired thioamide, 34.8 g (75% yield), as an orange solid, m.p. 123°–124° C.

B. 2-(N-acetylaminomethyl)-4-(indol-3'-yl)thiazole

A solution of 26.3 g of 3-chloroacetylindole and 17.9 g of the compound of Example 1A in 1500 ml of ethanol was heated to reflux overnight. The solvent was removed in vacuo and the residue triturated with methanol-chloroform (1:9-v:v) and filtered. The filtrate was concentrated and the crude residue was subjected to flash column chromatography on silica gel using methanol-chloroform (1:9-v:v) as the eluant to give 19 g (51% yield) of product.

C. 2-(aminomethyl)-4-(indol-3'-yl)thiazole hydrochloride

A mixture of 19 g of the product of Example 1B in 350 ml of concentrated hydrochloric acid was heated to reflux for three hours. The reaction mixture was cooled overnight and the precipitated product filtered. The solids were treated with 40 ml of ethanol followed by 350 ml of diethyl ether. The tan solid was filtered and dried, 12.5 g (67% yield), m.p. >250° C. D. 2-(guanidinomethyl)-4-(indol-3'-yl)thiazole hydrochloride A mixture of 2.5 g of the product of Example 1C, 12.2 g of 2-methyl-2-thiopseudourea sulfate and 7.71 g of sodium acetate in 300 ml of isopropanol was heated to reflux overnight. The reaction mixture was cooled, filtered and the filter cake washed with isopropanol. The filtrate and washings were combined, concentrated and the residue flash column chromatographed on 500 g of silica gel using methanol-chloroform (3:1-v:v) as the eluant. The resulting brown oil was dissolved in aceton and treated with 3 ml of concentrated hydrochloric acid. The resulting precipitate was filtered, washed with acetone and dried in vacuo, 2.34 g (83% yield), m.p. 231-234° C. (dec.).

The NMR spectrum (DMSO-d6) showed absorption at 4.84 (m, 2H), 7.13 (m, 2H), 7.44 (d, J=8.0 Hz, 1H), 7.74 (s, 1H), 7.86 (s, 1H) and 8.10 (d, J=8.0 Hz, 1H) ppm.

Employing the procedure of Example 1, and starting with the appropriate reagents, the following products were prepared:

$$\text{Ar}-\text{Het}-\text{CH}_2-\overset{H}{N}-\overset{\overset{\displaystyle NH}{\|}}{C}-NH_2$$

| Ar | Het | NMR(δ) |
|---|---|---|
| 4-ClC$_6$H$_4$— | thiazole | (DMSO-d$_6$) 4.61(s, 2H), 7.50(3, J=7Hz, 2H), 7.96(d, J=7Hz, 2H), 8.06(s, 1H). |
| 4-CH$_3$OC$_6$H$_4$— | thiazole | (DMSO-d$_6$) 3.81(s, 3H), 4.56(s, 2H), 6.98(d, J=7Hz, 2H), 7.80(s, 1H), 7.86 (d, J=7Hz, 2H). |
| 4-CH$_3$C$_6$H$_4$— | thiazole | (DMSO-d$_6$) 2.35(s, 3H), 4.62(s, 2H), 7.25(d, J=6Hz, 2H), 7.84(d, J=6Hz, 2H), 7.92(s, 1H). |
| 2-naphthyl | thiazole | (CDCl$_3$) 4.75(d, 2H), 7.45(m, 1H), 7.6 (bt, 4H), 7.9–8.1(m, 3H), 8.2(d, 1H), 8.25(s, 1H), 8.4–8.6(d, 2H). |
| 4-FC$_6$H$_4$— | thiazole | (DMSO-d$_6$) 4.43(s, 2H), 7.26(t, J=8Hz, 2H), 8.00(t J=8Hz, 2H), 8.13(s, 1H). |
| 2,4-(CH$_3$O)$_2$C$_6$H$_3$— | thiazole | (DMSO-d$_6$) 3.86(s, 3H), 3.96 (s, 3H), 4.73(s, 2H), 6.65(d, J=8Hz, 1H), 6.70(s, 1H), 7.86(s, 1H), 8.08(d, J=8Hz, 1H). |
| 2-CH$_3$OC$_6$H$_4$— | thiazole | (DMSO-d$_6$) 3.97(s, 3H), 4.71(s, 2H), 7.07(t, J=6Hz, 1H), 7.17(d, J=6Hz, 1H), 7.36(t, J=6Hz, 1H), 8.04(s, 1H), 8.16(d, J=6Hz, 1H). |
| CH$_3$— | thiazole | (DMSO-d$_6$) 2.38(s, 3H), 4.58(s, 2H), 7.16(s, 1H). |
| 2-methyl-1H-indol-3-yl | thiazole | (DMSO-d$_6$) 2.74(s, 3H), 4.52(s, 2H), 7.13(m, 2H), 7.40(d, J=6Hz, 1H), 7.44(s, 1H), 8.02(d, J=6Hz, 1H). |
| 1-benzyl-1H-indol-3-yl | thiazole | (DMSO-d$_6$) 4.80(s, 2H), 5.45(s, 2H), 6.60(s, 5H), 7.1–7.3(m, 3H), 7.5 (d, 1H), 7.72(s, 1H), 7.95(s, 1H). |
| 1-methyl-1H-indol-3-yl | thiazole | (CD$_3$OD) 3.88(s, 3H), 4.70(s, 2H), 7.16(t, J=6Hz, 1H), 7.24(t, J=6Hz, 1H), 7.42(d, J=6Hz, 1H), 7.48(s, 1H), 7.67(s, 1H), 8.00(J=6Hz, 1H). |

Employing the procedure of Example 1, and starting with the appropriate reagents, the following products were prepared:

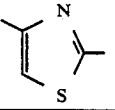

| Ar | Het | NMR(δ) |
|---|---|---|
| $C_6H_5-$ | 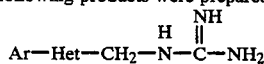 | (DMSO-$d_6$) 4.82(s, 2H), 7.37(m, 1H), 7.46(t, J=8Hz, 2H), 7.95(d, J=8Hz, 2H), 8.08(s, 1H). |

EXAMPLE 3

2-(2''-Imidazolinylaminomethyl)-4-(indol-3'-yl)thiazole (Ar=indol-3-yl; Het=thiazolyl; $R_1$=H and $R_2$, $R_3$=—$CH_2CH_2$—)

To a mixture of 133 mg of the product of Example 1C in 5 ml of isopropanol were added 610 mg of 2-methylthioimidazoline hydroiodide and 410 mg of sodium acetate and the resulting reaction mixture heated at 90° C. for two hours. The reaction mixture was cooled to room temperature and concentrated in vacuo to dryness, the residue was triturated with 2N aqueous sodium hydroxide and chloroform and decanted. The residue remaining was dissolved in methanol. The methanol was dried and concentrated to give the desired product as a tan solid, 40 mg.

The NMR spectrum (DMSO-$d_6$) showed absorption at 3.4 (m, 4H), 4.65 (bs, 2H), 7.15 (m, 2H), 7.42 (d, J=8 Hz, 1H), 7.61 (s, 1H), 7.84 (s, 1H) and 8.09 (d, J=8 Hz, 1H) ppm.

EXAMPLE 4

2-($N_3$-Hydroxyethylguanidinomethyl)-4-(indol-3'-yl)thiazole (Ar=indol-3-yl; Het=thiazolyl; $R_1$ and $R_2$=H; and $R_3$=HOCH$_2$CH$_2$—)

A. 2-($N_2$-cyano-S-methylthiospeudoureido)4-(indol-3'-yl)thiazole

To a suspension of 1.0 g of the product of Example 1C and 522 mg of potassium carbonate in 10 ml of ethanol and 3 ml of water was added dropwise 613 mg of dimethyl cyanodithioimiocarbonate in 10 ml of ethanol over a period of ten minutes. The reaction mixture was stirred overnight at room temperature and was treated with diethyl ether. The resulting tan solid was filtered, washed with water and diethyl ether and dried, 710 mg. Removal of the solvent from the filtrate provided an additional 300 mg of product.

B. 2-($N_2$-cyano-$N_3$-hydroxyethylguanidinomethyl)4-(indol-3'-yl)thiazole

To a suspension of 100 mg of the product of Example 4A in 1 ml of ethanol was added 0.98 ml of aminoethanol and the resulting reaction mixture heated to 50° C. for four hours. The solvent was removed in vacuo and the residue triturated with diethyl ether and ethyl acetate to give 102 mg of a yellow oil.

C. 2-($N_3$-hydroxyethylguanidinomethyl)-4-(indol-3'-yl)thiazole

The product of Example 4B (102 mg) was added to 2 ml of concentrated hydrochloric acid and the reaction mixture stirred overnight at room temperature. The solvent was removed in vacuo and the residue was triturated with 2N sodium hydroxide and then water. The solvent was removed in vacuo and the solids dried at oven temperature overnight. The solids were triturated with diethyl ether and filtered, 35 mg, m.p. >250° C.

The NMR spectrum (DMSO-$d_6$) showed absorption at 3.22 (m, 2H), 3.52 (t, J=4 Hz, 2H), 4.57 (s, 2H), 7.14 (m, 2H), 7.45 (d, J=7 Hz, 1H), 7.61 (s, 1H), 7.83 (s, 1H) and 8.10 (d, J=7 Hz, 1H).

EXAMPLE 5

Using the procedures of Example 4 and starting with the appropriate reagents, the following analogs were prepared:

| $R_3$ | NMR(δ) |
|---|---|
| $CH_3—$ | (DMSO-$d_6$) 2.80(s, 3H), 4.82(s, 2H), 7.10(m, 2H), 7.38(m, 1H), 7.41(d, J=6Hz, 1H), 7.72(s, 1H), 7.83(s, 1H), 8.07(d, J=6 Hz, 1H). |
|  | (DMSO-$d_6$) 0.61(m, 2H), 0.85(m, 3H), 4.87(s, 2H), 7.12(m, 2H), 7.44(d, J=7Hz, 1H), 7.66(s, 1H), 7.84(s, 1H), 8.10(d, J=7 Hz, 1H). |
| —(CH$_2$)$_5$CH$_3$ | (DMSO-$d_6$) 0.84(m, 3H), 1.25(m, 6H), 1.49(m, 2H), 3.19(m, 2H), 4.84(s, 2H), 7.11(m, 2H), 7.42 (d, J=7Hz, 1H), 7.72(s, 1H), 7.83(s, 1H), 8.08(d, J=7Hz, 1H). |
| —(CH$_2$)$_3$CH$_3$ | (DMSO-$d_6$) 0.89(t, J=9Hz, 3H), 1.33(m, 2H), 1.51(m, 2H), 3.22 (m, 2H), 4.88(m, 2H), 7.14(m, 2H), 7.37(d, J=6Hz, 1H), 7.44 (d, J=6Hz, 1H), 7.54(d, J=6Hz, 1H), 7.86(s, 1H), 8.11(d, J=6 Hz, 1H). |

EXAMPLE 6

2-($N_1$-Methylguanidinomethyl)-4-(indol-3'-yl)thiazole (Ar=indol-3-yl; Het=thiazolyl; $R_1$=CH$_3$; and $R_2,R_3$=H)

A. N-acetyl-N-methylaminoacetonitrile

To a cold (0° C.) solution of 15 g of N-methylaminoacetonitrile hydrochloride and 5.63 g of sodium hydroxide in 66 ml of water was added dropwise over twenty minutes 26.5 ml of acetic anhydride. The ice bath was removed and the reaction mixture stirred for several days at room temperature. The solvent was removed in vacuo and the residue triturated with chloroform. The solids were filtered and the filtrate concentrated to give the desired product, 18.03 g, as a yellow oil.

B. N-acetyl-N-methylaminothioacetamide

To 24 ml of dimethylformamide saturated with hydrogen chloride gas was added 8.03 g of the product of Example 6A and 10.76 g of thioacetamide, and the reaction mixture heated to reflux for 125 hours. The solvent was removed in vacuo and the residue triturated with diethyl ether. The ether was decanted and the residual oil chromatographed on 400 g of silica gel using initially ethyl acetate-chloroform (1:3-v:v) followed by methanol-chloroform (1:19-v:v) to give 1.71 g of the desired intermediate.

C. 2-(N-acetyl-N-methylaminomethyl)4-(indol-3'-yl)thiazole

Using the procedure of Example 1B, 3-chloroacetylindole and 2.56 g of the product of Example 6B in 150 ml of ethanol gave 870 mg of the named product.

D. 2-(N-methylaminomethyl)-4-(indol-3'-yl)thiazole hydrochloride

Using the procedure of Example 1C, 870 mg of the product of Example 6C in 12 ml of concentrated hydrochloric acid gave 776 mg of the named product.

E. 2-($N_1$-methylguanidinomethyl)4-(indol-3'-yl)thiazole

Employing the procedure of Example 1D, 152 mg of the product of Example 6D, 777 mg of 2-methyl-2-thiopseudourea sulfate and 550 m of sodium acetate in 10 ml of isopropanol gave 159 mg of the final product as the free base.

The NMR spectrum (DMSO-$d_6$) showed absorption at 2.89 (s, 3H), 4.80 (s, 2H), 7.11 (m, 2H), 7.42 (d, J=7 Hz, 1H), 7.64 (s, 1H), 7.82 (s, 1H) and 8.09 (d, J=7 Hz, 1H) ppm.

EXAMPLE 7

3-(2'-Naphthyl)-5-(guanidinomethyl)isoxazole
(Ar=2-naphthyl; Het=isoxazolyl; and $R_1,R_2$ and $R_3$=H)

A. 2-naphthalaldehyde oxime

To a mixture of 7.8 g of 2-naphthalaldehyde and 7.1 ml of triethylamine in 100 ml of methylene chloride was added 3.54 g of hydroxylamine hydrochloride and the mixture heated at 35° C. for three hours. The organic reaction solvent was washed with water, dried and concentrated to give 8.4 g of product.

B. 2-naphthoyl chloride oxime

Chlorine gas was bubbled into a suspension of 5 g of the oxime of Example 7A in 150 ml of chloroform until the blue-green color initially produced turned to yellow (about one hour). The solids were filtered and the filtrate concentrated to 50 ml. The addition of petroleum ether precipitated the product which was filtered and dried, 1.3 g.

C. 3-(2'-naphthyl)-5-aminomethylisoxazole

To a solution of 410 mg of the product of Example 7B in 5 ml of benzene at 10° C. was added dropwise 0.68 ml of propargylamine followed by 0.029 ml of triethylamine. The reaction mixture was stirred at 10° C. for thirty minutes and then allowed to warm to room temperature. The reaction was quenched in water, the pH adjusted to 9 with aqueous sodium hydroxide and the benzene layer separated and dried. Removal of the benzene in vacuo gave 400 g of crude product which was purified by flash chromatography on ten grams of silica gel using chloroform-methanol (10:1-v:v) as the eluant, 100 mg.

D. 3(2'-naphthyl-5-(guanidinomethyl)isoxazole

Using the procedure of Example 1D, 50 mg of the product of Example 7C, 280 mg of the thiourea and 180 mg of sodium acetate in 5 ml of isopropanol gave 40 mg of product.

The NMR spectrum (CDCl$_3$) showed absorption at 4.55 (s, 2H), 6.67 (s, 1H), 7.24 (s, 1H), 7.42 (m, 2H), 7.55 (m, 3H) and 8.1 (s, 1H) ppm.

EXAMPLE 8

2-(Guanidinomethyl)-5-(2'-naphthyl)thiophene
(Ar=2-naphthyl; Het=thienyl; and $R_1,R_2$ and $R_3$=H)

A. 2-(aminomethyl)-5-(2'-naphthyl)thiophene

To a cooled (5° C.) solution of 2-aminonaphthalene in 6 ml of 2N hydrochloric acid was added dropwise over ten minutes a solution of 350 mg of sodium nitrite in 1 ml of water followed by the dropwise addition of 680 mg of zinc chloride in 5 ml of water over a period of fifteen minutes. After stirring for two hours, the solids were filtered, washed with ethyl acetate, hexane and, finally, acetone. The intermediate diazonium salt was dried, 600 mg.

To a solution of 2-aminomethylthiophene (0.36 ml) and triethylamine (0.69 ml) in 10 ml of methylene chloride was added 0.39 ml of trimethylsilyl chloride and the reaction mixture stirred at room temperature for thirty minutes. To the reaction mixture was added 50 m of powdered sodium hydroxide, 500 mg of sodium acetate and 600 mg of the above-identified diazonium salt and the mixture stirred at room temperature for eighteen hours. The reaction mixture was quenched in water, the pH adjusted to 9 with aqueous sodium hydroxide and the organic layer separated. Removal of the solvent gave 600 mg of crude product which was purified by flash chromatography on 15 g of silica gel using chloroform as the eluant, 110 mg.

B. 2-(guanidinomethyl)-5-(2'-naphthyl)thiophene

Using the procedure of Example 1D, 70 mg of the product of Example 8A, 400 mg of the thiourea and 240 mg of sodium acetate in 10 ml of isopropanol gave 30 mg of the named product.

The NMR spectrum (CDCl$_3$) showed absorption at 4.65 (s, 2H), 6.7(m, 1H), 6.75 (m, 1H), 6.75–7.15 (m, 2H), 7.25–7.45 (m, 1H), 7.52 (m, 1H), 7.7–7.9 (m, 2H) and 8.2 (d, 1H) ppm.

EXAMPLE 9

2-(Guanidinomethyl)-5-(2'-naphthyl)furan
(Ar=2-naphthyl; Het=furyl; and $R_1,R_2$ and $R_3$=H)

A. 2-(2'naphthyl)furan-5-carboxaldehyde

To cold dimethylformamide (5 ml), 5°–10° C., was added 1.3 ml of phosphorus oxychloride, keeping the temperature below 15° C., followed by 2.0 g of 2-(2'-naphthyl)furan [*J. Chem. Soc.*, (Perkin) 2327 (1973)] in 5 ml of the same solvent dropwise over ten minutes. The reaction mixture was heated at 40° C. for thirty minutes and was then allowed to cool to room temperature. Water and ice were added to the reaction mixture and the mixture cooled. The yellow precipitate was filtered and air-dried, 1.58 g.

B. 2-(2'-naphthyl)furan-5-carboxaldehyde oxime

A solution of 800 mg of the product of Example 9A, 280 mg of hydroxylamine hydrochloride and 55 ml of triethylamine in 20 ml of chloroform was stirred at room temperature for eighteen hours. The reaction mixture was added to water and the organic phase separated, dried and concentrated to dryness, 700 mg.

C. 2-(2'-naphthyl)-5-(aminomethyl)furan

A mixture of 700 mg of the product of Example 9B, 400 mg of zinc dust and 15 ml of acetic acid were stirred at room temperature for eighteen hours. The solids were filtered and the filtrate concentrated in vacuo to an oil. The residue was partitioned between ethyl acetate and water and the pH adjusted to pH 9.5 with sodium carbonate. The organic phase was separated and combined with water and the pH adjusted to 1.9 with 1N hydrochloric acid. The aqueous layer was separated, made basic to pH 10.0 and extracted with ethyl acetate. The organic phase was separated, dried and concentrated to give 130 mg of the named product.

D. 2-(guanidinomethyl)-5-(2'-naphthyl)furan hydrochloride

Using the procedure of Example 1D, 130 mg of the product of Example 9C, 800 mg of the pseudothiourea and 480 mg of sodium acetate in 20 ml of isopropanol gave 4 mg of the desired product.

The NMR spectrum (CDCl$_3$) showed absorption at 4.30 (bs, 2H), 6.30 (d, 1H), 6.40 (d, 1H), 7.30 (m, 2H), 7.45 (d, 1H), 7.55–7.70 (m, 3H) and 7.8 (s, 1H) ppm.

EXAMPLE 10

2-(Indol-3'-yl)-4-(guanidinomethyl)thiazole hydrochloride (Ar=indol-3-yl; Het=thiazolyl; and R$_1$,R$_2$, and R$_3$=H)

A. indole-3-thioamide hydrochloride

To a solution of 1.0 g of 3-cyanoindole in 30 ml of ethyl acetate was added 1.1 ml of diethyldithiophosphonic acid. The solution was then saturated with gaseous hydrogen chloride and stirred at room temperature for 18 hours. The thioamide was isolated from the reaction mixture as a tan precipitate and used directly in the following reaction.

B. 2-(indol-3'-yl)-4-(phthalimidomethyl)thiazole hydrochloride

A suspension of 0.4 g of phthalimidomethyl chloromethyl ketone and 0.3 g of the thioamide of Example 10A in 25 ml of isopropanol was refluxed for 4 hours. The suspension gradually became a clear solution, followed by the precipitation of a new solid. The reaction mixture was cooled to room temperature and filtered to yield 0.41 g of the thiazole hydrochloride salt.

C. 2-(indole-3'-yl)-4-(aminomethyl)thiazole

A solution of 0.4 g of the product of Example 10B and 0.32 ml of hydrazine in 30 ml of methanol was stirred at room temperature for 18 hours. A white precipitate separated from the reaction mixture. The reaction mixture was filtered and the filtrate evaporated to afford the crude amine. Trituration of amine with ethyl acetate afforded 0.15 g of pure product.

D. 2-(indol-3'-yl)-4-(guanidinomethyl)thiazole hydrochloride

A mixture of 0.15 g of the product of Example 10C, 0.9 g of 2-methyl-2-thiopseudourea sulfate, and 0.5 g of sodium acetate in 50 mol of isopropanol was refluxed for 2.5 hours. The reaction mixture was cooled to room temperature and evaporated. The residue was triturated with ethyl acetate and recrystallized from hot isopropanol to yield 0.16 g of product.

The NMR spectrum (DMSO-d$_6$) showed absorption at 8.15 (d, 1H), 8.10 (s, 1H), 7.50 (d, 1H), 7.38 (s, 1H), 7.20 (m, 2H) and 4.55 (br.s, 2H) ppm.

EXAMPLE 11

4-(Indol-3'-yl)-2-(N$_2$,N$_3$-diacetylguanidinomethyl)-thiazole (Ar=indol-3-yl; Het=thiazolyl; R$_1$=H; and R$_2$ and R$_3$=CH$_3$CO—)

A mixture of 300 mg of the product of Example 1 and 0.37 ml of acetic anhydride in 5 ml of pyridine was stirred at room temperature overnight. The reaction mixture was added to a mixture of methylene chloride and a saturated aqueous sodium bicarbonate solution. The organic phase was collected and additional methylene chloride was used to further extract the aqueous phase. The organic extracts were combined, dried over sodium sulfate and concentrated. The residual oil was flash chromatographed to obtain 34 mg of product, m.p. 175° C.

The NMR spectrum (CDCl$_3$) showed absorption at 2.20 (s, 3H), 2.22 (s, 3H), 4.99 (d, J=6 Hz, 2H), 7.24 (m, 2H), 7.34 (s, 1H), 7.40 (m, 1H), 7.76 (d, J=2 Hz, 1H) and 8.02 (m, 1H) ppm.

EXAMPLE 12

4-(Indol-3'-yl)-2-(N$_2$-acetylguanidinomethyl)thiazole (Ar=indol-3-yl; Het=thiazolyl; R$_1$ and R$_3$=H; and R$_2$=CH$_3$CO—)

A mixture of the product of Example 11 and 0.8 ml of tetrahydrofuran in 0.8 ml of 2N aqueous sodium hydroxide was stirred at room temperature for 2 hours. The reaction mixture was diluted with water and the product extracted with methylene chloride. The extracts were combined, dried over sodium sulfate and concentrated to give 25 mg of product, m.p. 115°–117° C.

The NMR spectrum (CDCl$_3$) showed absorption at 2.21 (s, 3H), 4.74 (s, 2H), 7.26 (m, 2H), 7.39 (s, 1H), 7.47 (m, 1H), 7.68 (s, 1H), and 7.96 (m, 1H) ppm.

What is claimed is:

1. A compound of the formula

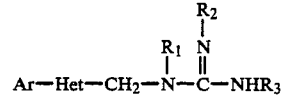

or a pharmaceutically acceptable acid addition salt thereof, wherein Ar is naphthyl, indol-3-yl, 2-methylindol-3-yl, 1-methylindol-3-yl, 1-benzylindol-3-yl phenyl, or mono- or disubstituted phenyl wherein said substituent is each methyl, methoxy, chloro, fluoro or bromo; Het is 4-thiazol-2-yl, 3-isoxazol-5-yl, 2-thien-5-yl or 2-fur-5-yl; R$_1$ is hydrogen or methyl; R$_2$ and R$_3$ when considered separately are each hydrogen, hydroxyethyl, alkyl having one to six carbon atoms, cycloalkyl having three to six carbon atoms or acetyl; and R$_2$ and R$_3$ when taken together are alkylene having two to three carbon atoms.

2. A compound of claim 1, wherein Het is 4-thiazol-2-yl and R$_1$, R$_2$ and R$_3$ are each hydrogen.

3. The compound of claim 2, 2-(guanidinomethyl)-4-(1'-methylindol-3'-yl)thiazole.

4. The compound of claim 2, 2-(guanidinomethyl)-4-(o-methoxyphenyl)thiazole.

5. The compound of claim 2, 2-(guanidinomethyl)-4-(2'-methylindol-3'-yl)thiazole.

6. The compound of claim 2, 2-(guanidinomethyl)-4-(indol-3'-yl)thiazole.

7. The compound of claim 2, 2-(guanidinomethyl)-4-phenylthiazole.

8. The compound of claim 2, 2-(indol-3'-yl)-4-(guanidinomethyl)thiazole.

9. The compound of claim 2, 2-(guanidinomethyl)-4-(o-fluorophenyl)thiazole.

* * * * *